(12) United States Patent
Hong

(10) Patent No.: US 9,131,954 B2
(45) Date of Patent: Sep. 15, 2015

(54) SAFETY LANCET FOR DOUBLY PREVENTING REUSE THEREOF

(75) Inventor: Kwan Ho Hong, Gyeonggi-do (KR)

(73) Assignee: GMMC INC., Seoul (KR)

( * ) Notice: Subject to any disclaimer, the term of this patent is extended or adjusted under 35 U.S.C. 154(b) by 433 days.

(21) Appl. No.: 13/635,231

(22) PCT Filed: Jul. 3, 2012

(86) PCT No.: PCT/KR2012/005282
§ 371 (c)(1),
(2), (4) Date: Sep. 14, 2012

(87) PCT Pub. No.: WO2013/015538
PCT Pub. Date: Jan. 31, 2013

(65) Prior Publication Data
US 2013/0066353 A1    Mar. 14, 2013

(30) Foreign Application Priority Data

Jul. 26, 2011  (KR) .................... 10-2011-0073954
Jan. 3, 2012   (KR) .................... 10-2012-0000433

(51) Int. Cl.
*A61B 17/3209* (2006.01)
*A61B 5/15* (2006.01)
*A61B 5/151* (2006.01)

(52) U.S. Cl.
CPC .......... *A61B 17/3209* (2013.01); *A61B 5/1411* (2013.01); *A61B 5/1513* (2013.01); *A61B 5/15016* (2013.01); *A61B 5/150022* (2013.01); *A61B 5/15109* (2013.01); *A61B 5/15113* (2013.01); *A61B 5/15117* (2013.01);

(Continued)

(58) Field of Classification Search
CPC ............ A61B 17/3207; A61B 5/1411; A61B 5/150022; A61B 5/150412; A61B 5/15117; A61B 5/150717; A61B 5/150885; A61B 5/15144; A61B 5/15142
USPC ......................................................... 606/162
See application file for complete search history.

(56) References Cited

U.S. PATENT DOCUMENTS 5,366,470 A * 11/1994 Ramel ........................... 606/183
5,628,764 A *  5/1997 Schraga ........................ 606/182

(Continued)

*Primary Examiner* — Thomas McEvoy
*Assistant Examiner* — Julie A Szpira
(74) *Attorney, Agent, or Firm* — Rabin & Berdo P.C.

(57) ABSTRACT

Provided is a safety lancet including a reload double prevention structure for preventing a sliding block having a lancet needle from being reloaded to obtain blood, thereby fundamentally preventing reuse of the safety lancet. In addition, the safety lancet guides the sliding block to be straightly discharged without shaking, thereby minimizing pain when the lancet needle is inserted into a skin. The safety lancet includes an outer case forming a space part therein, an inner case sliding along the space part of the outer case, and having a through hole in a front end thereof, and a sliding block coupled to the inner case to straightly move along an inner portion of the inner case, and elastically supported within the outer case by a coil spring, wherein the sliding block comprises a lancet needle having an end protruding from a front end thereof, and a pair of loading hooks on both sides of a rear end thereof to engage with engagement protrusions of the inner case. As the inner case is moved rearward, when the sliding block is disengaged from a portion of the inner case, the sliding block is moved forward by elastic force of the coil spring to temporarily expose the lancet needle out of the inner case, and is then moved rearward to the inner case.

15 Claims, 17 Drawing Sheets

(52) U.S. Cl.
CPC ....... *A61B5/15144* (2013.01); *A61B 5/150412* (2013.01); *A61B 5/150503* (2013.01); *A61B 5/150564* (2013.01); *A61B 5/150717* (2013.01); *A61B 5/150885* (2013.01)

(56) References Cited

U.S. PATENT DOCUMENTS

| | | | |
|---|---|---|---|
| 5,908,434 A * | 6/1999 | Schraga | 606/181 |
| 6,432,120 B1 * | 8/2002 | Teo | 606/182 |
| 6,613,064 B2 * | 9/2003 | Rutynowski et al. | 606/185 |
| 6,866,641 B2 * | 3/2005 | Marshall | 600/583 |
| 7,955,347 B2 * | 6/2011 | Stout | 606/181 |
| 8,172,867 B2 * | 5/2012 | Nicholls | 606/182 |
| 8,333,781 B2 * | 12/2012 | Karbowniczek et al. | 606/182 |
| 8,858,582 B2 * | 10/2014 | Schiff et al. | 606/181 |
| 2002/0087180 A1 * | 7/2002 | Searle et al. | 606/181 |
| 2004/0260326 A1 * | 12/2004 | Lipoma et al. | 606/182 |
| 2006/0259058 A1 * | 11/2006 | Schiff et al. | 606/181 |
| 2007/0203514 A1 * | 8/2007 | Flaherty et al. | 606/181 |
| 2008/0195132 A1 * | 8/2008 | Schraga | 606/182 |
| 2009/0287237 A1 * | 11/2009 | Nicholls | 606/182 |
| 2009/0299397 A1 * | 12/2009 | Ruan et al. | 606/182 |

* cited by examiner

SAFETY LANCET FOR DOUBLY PREVENTING REUSE THEREOF

BACKGROUND OF THE INVENTION

1. Field of the Invention

The present invention relates to a safety lancet, and more particularly, to a safety lancet for doubly preventing reuse thereof, which is fundamentally prevented from being reused for obtaining blood, thereby preventing transmission of diseases.

2. Description of the Related Art

Lancets are used to conveniently take blood from patients to be variously treated in a hospital. For example, a lancet may be inserted into a subcutaneous tissue of a finger or toe to take a small amount of blood from a capillary vessel, and the taken blood may be used to measure a patient's blood sugar, cholesterol, or triglycerides (TG) by using a hemanalysis device.

However, typical lancets may be reused just by washing or sterilizing the lancets after taking blood. Accordingly, various diseases such as AIDS or hepatitis may be transmitted through a patient's blood, which causes serious medical accidents.

Thus, safety lancets should be used only once to prevent such transmission of diseases. However, typical safety lancets can be reused through a simple disassembly and assembly process.

Korean Patent Registration No. 971171 discloses a safety lancet for preventing reuse as illustrated in FIG. 30.

Such a typical safety lancet includes: an upper case 1 and a lower case 2, which form an inner space having a certain size; a movable block 3 disposed within the inner space and having a spring 6; and a guide 4 as a trigger disposed at the rear end thereof.

An operation of the safety lancet for taking blood is as follows. When an outer pressing plate 5 is pressed by a finger, pressing force is transmitted to the lower part of the guide 4 through the outer pressing plate 5 so as to release a hook of the movable block 3. At this point, the movable block 3 is moved forward by elastic force of the spring 6, and a lancet needle 7 disposed at the front end of the movable block 3 is quickly inserted into a skin and is removed therefrom. A protective cap 8 encloses the lancet needle 7 before the safety lancet is used.

Since the guide 4 functioning as a trigger is exposed out of the safety lancet, when a user accidentally presses the outer pressing plate 5, the movable block 3 may be discharged, which is dangerous.

In addition, after the movable block 3 is discharged, the movable block 3 may be reloaded by inserting a long rod through a front through hole, or disassembling and assembling the safety lancet, whereby the safety lancet may be intentionally reused.

Furthermore, the safety lancet is required to reduce a pain caused when the lancet needle 7 is inserted into a skin. To this end, not only the performance or diameter of a needle is adjusted, but also the movable block 3 is required to be straightly discharged under a uniform condition, without shaking or vibration caused by the spring 6.

SUMMARY OF THE INVENTION

An object of the present invention is to provide a safety lancet including a structure for preventing a sliding block having a lancet needle from being reloaded to obtain blood, thereby fundamentally preventing reuse of the safety lancet.

Another object of the present invention is to provide a safety lancet guiding a sliding block to be straightly discharged without shaking, thereby minimizing pain when a lancet needle is inserted into a skin.

According to an aspect of the present invention, there is provided a safety lancet including: an outer case forming a space part therein; an inner case sliding along the space part of the outer case, and having a through hole in a front end thereof; and a sliding block coupled to the inner case to straightly move along an inner portion of the inner case, and elastically supported within the outer case by a coil spring, wherein the sliding block comprises a lancet needle having an end protruding from a front end thereof, and a pair of loading hooks on both sides of a rear end thereof to engage with engagement protrusions of the inner case, wherein as the inner case is moved rearward, when the sliding block is disengaged from a portion of the inner case, the sliding block is moved forward by elastic force of the coil spring to temporarily expose the lancet needle out of the inner case, and is then moved rearward to the inner case by resilient force of the coil spring.

To doubly prevent reloading of the sliding block, the inner case may include a pair of reload prevention hooks on both sides of a rear end thereof, and the outer case may include catching protrusions on both sides of an inner portion thereof to catch the reload prevention hooks of the inner case.

The inner case may include: a pair of coupling hooks on both the sides of the rear end thereof to couple to the outer case; and a pair of guide holders on outer top and bottom surfaces thereof, respectively, wherein each of the guide holders comprises a pair of trigger catchers, and the outer case may include guide ribs on outer top and bottom surfaces thereof to guide the trigger catchers of the inner case, wherein trigger protrusions are disposed on rear ends of the guide ribs, and are caught by the trigger catchers of the inner case.

When the inner case is moved rearward such that the trigger catchers are moved along the guide ribs and are disengaged from the trigger protrusions of the outer case, the elastic force of the coil spring may be applied to the sliding block to disengage the loading hooks of the sliding block from the engagement protrusions of the inner case.

A pair of loading release guide recesses may be disposed in the outer case, wherein when the sliding block is moved rearward within a certain time after the inner case is moved rearward, the loading release guide recesses guide the loading hooks of the sliding block to decrease a distance therebetween, thereby disengaging the loading hooks from the engagement protrusions of the inner case.

The sliding block may include first to fourth guide rails on four outer surfaces thereof, respectively, and the inner case may include first to fourth guide recesses in the inner portion thereof, wherein the first to fourth guide rails are slidably coupled to the first to fourth guide recesses.

When the inner case is moved rearward such that the trigger catchers are moved along the guide ribs and are disengaged from the trigger protrusions of the outer case, the elastic force of the coil spring may be applied to the sliding block to break neck parts of the loading hooks of the sliding block, thereby disengaging the loading hooks of the sliding block from the engagement protrusions of the inner case.

Edges of the loading hooks may be rounded, and edges of the engagement protrusions engaging with the loading hooks may be rounded, wherein when the inner case is moved rearward such that the trigger catchers are moved along the guide ribs and are disengaged from the trigger protrusions of the outer case, the elastic force of the coil spring is applied to the sliding block to slide the edges of the loading hooks along the edges of the engagement protrusions, thereby disengaging the loading hooks of the sliding block from the engagement protrusions of the inner case.

A guide rod having a rod shape, which is inserted in the coil spring and is slidably coupled to the outer case, may be integrally formed with the rear end of the sliding block to prevent shaking and vibration of the sliding block when being discharged, and a spring fixing recess may be disposed inside of the outer case such that an end of the coil spring is inserted and fixed in the spring fixing recess.

The inner case may include: a pair of coupling hooks on both the sides of the rear end thereof to couple to the outer case; and a pair of guide holders on outer top and bottom surfaces thereof, respectively, wherein each of the guide holders comprises a pair of trigger catchers, and the outer case may include guide ribs on outer top and bottom surfaces thereof to guide the trigger catchers of the inner case, wherein trigger protrusions are disposed on rear ends of the guide ribs, and are caught by the trigger catchers of the inner case. In this case, a guide rod having a rod shape, which is inserted in the coil spring and is slidably coupled to the outer case, may be integrally formed with the rear end of the sliding block to prevent shaking and vibration of the sliding block when being discharged, and a spring fixing recess may be disposed inside of the outer case such that an end of the coil spring is inserted and fixed in the spring fixing recess.

In this case, the outer case may include an operation button on a rear end thereof to press the guide rod and move the sliding block forward, and the forward movement of the sliding block may break neck parts of the loading hooks of the sliding block, thereby disengaging the loading hooks of the sliding block from the engagement protrusions of the inner case.

The outer case may include a pair of operation buttons extending from both sides thereof and elastically connected thereto, and the operation buttons may press the loading hooks to decrease a distance therebetween, thereby disengaging the loading hooks from catching protrusions disposed on both sides of the inner case.

After moving forward, the sliding block may be returned into the inner case by the resilient force of the coil spring to retract the lancet needle into the inner case.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Hereinafter, a safety lancet for preventing reuse according to first to fifth embodiments will be described with reference to the accompanying drawings. Detailed descriptions related to well-known functions or configurations will be ruled out in order not to unnecessarily obscure subject matters of the present invention.

Figure 1:
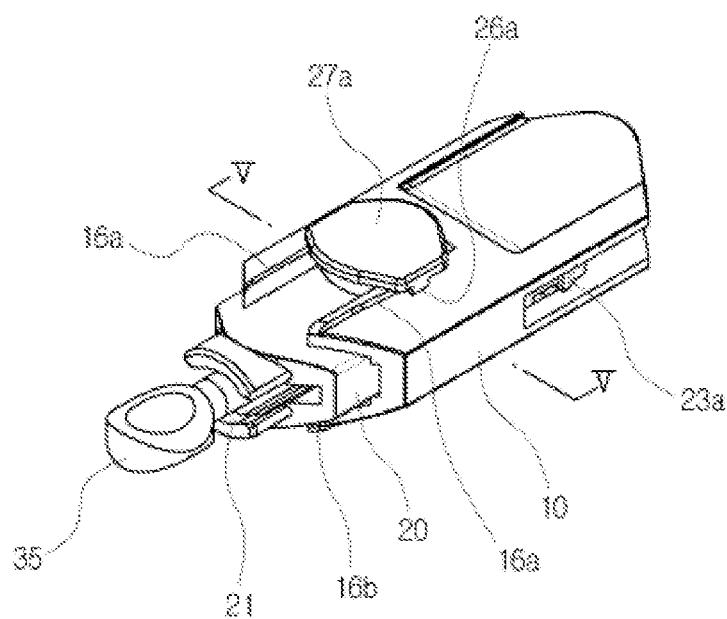
FIG. 1 is a perspective view illustrating a safety lancet according to a first embodiment of the present invention.
Figure 2:
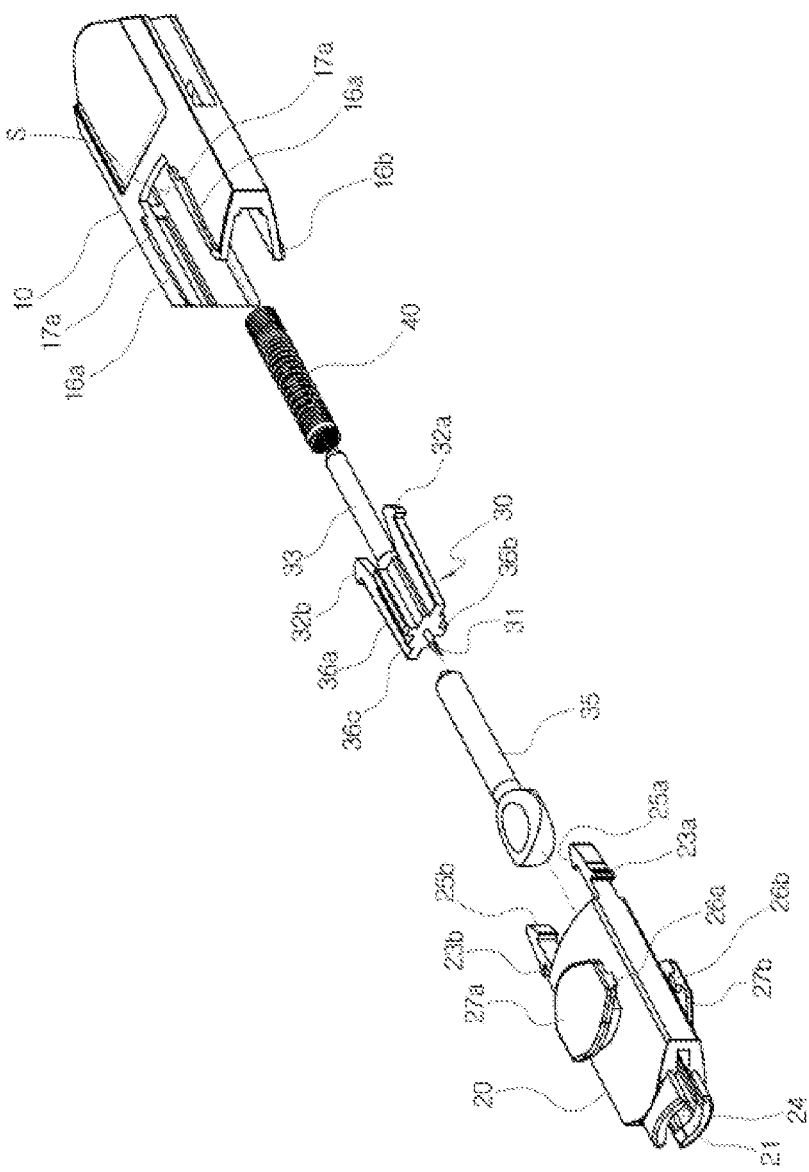
FIG. 2 is an exploded perspective view illustrating the safety lancet according to the first embodiment of the present invention.

Referring to FIG. 1, a safety lancet according to the first embodiment includes an outer case 10, an inner case 20, and a sliding block 30 (refer to FIG. 2).

Figure 3:
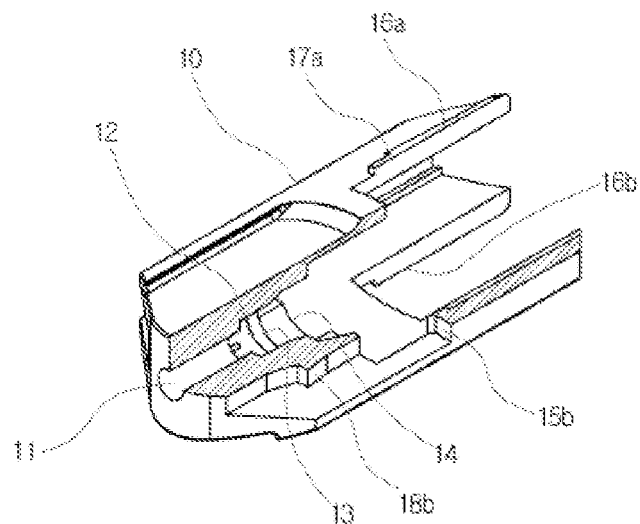
FIG. 3 is a partial cut-away perspective view illustrating an outer case of FIG. 2.

Referring to FIGS. 2 and 3, the outer case 10 forms a space part S therein, and the inner case 20 is slidably coupled to the space part S. A guide hole 11 is disposed in the rear end of the outer case 10. A guide rod 33 of the sliding block 30 is slidably inserted in the guide hole 11. A spring fixing recess 12 is disposed inside of the guide hole 11. An end of a coil spring 40 is inserted and fixed in the spring fixing recess 12.

The outer case 10 includes guide ribs 16a and 16b on an outer top surface and an outer bottom surface thereof to guide trigger catchers 26a and 26b of the inner case 20. Trigger protrusions 17a and 17b are disposed on the rear ends of the guide ribs 16a and 16b, and are engaged with the trigger catchers 26a and 26b, respectively.

Figure 4:
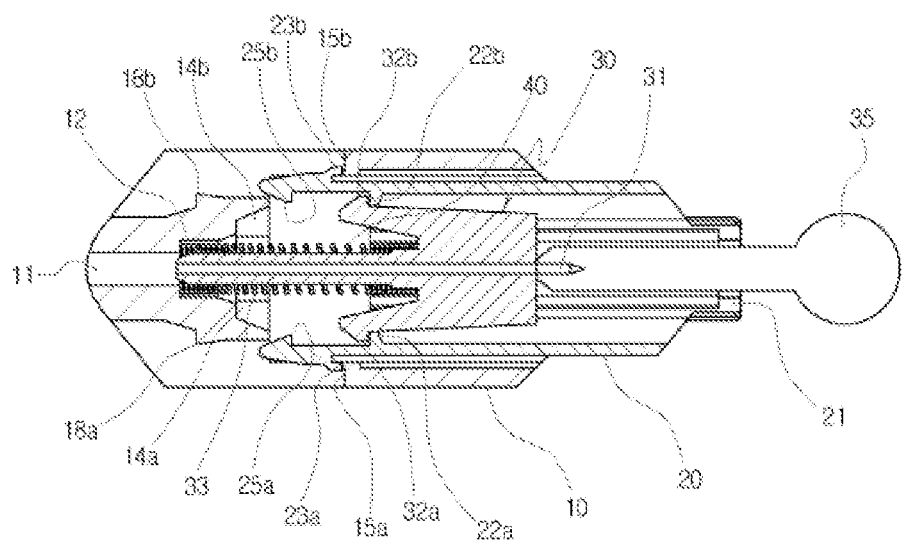
FIG. 4 is a cross-sectional view illustrating a state before the safety lancet is used, according to the first embodiment of the present invention.
Figure 8:
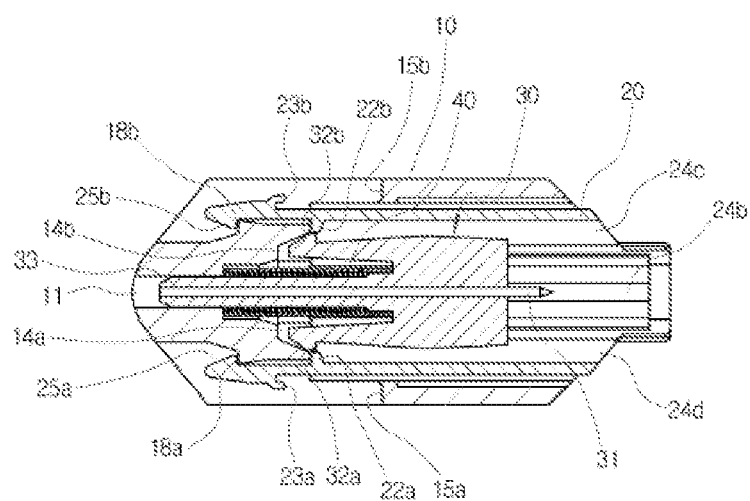

Referring to FIGS. 4 and 8, a pair of loading release guide recesses 14a and 14b are disposed in the outer case 10. When the sliding block 30 is moved rearward within a certain time after the inner case 20 is moved rearward, the loading release guide recesses 14a and 14b guide a pair of loading hooks 32a and 32b of the sliding block 30 to decrease the distance therebetween, thereby disengaging the loading hooks 32a and 32b from engagement protrusions 22a and 22b of the inner case 20.

Catching protrusions 18a and 18b are disposed at both inner sides of the outer case 10, respectively. Reload prevention hooks 25a and 25b of the inner case 20 are caught by the catching protrusions 18a and 18b.

Referring to FIGS. 2 and 4, the inner case 20 includes: a through hole 21 in the front part thereof through which a lancet needle 31 protrudes; the engagement protrusions 22a and 22b on both inner sides thereof, the loading hooks 32a and 32b being loaded on the engagement protrusions 22a and 22b; and a pair of coupling hooks 23a and 23b engaging with a pair of latch protrusions 15a and 15b of the outer case 10, respectively, to load the inner case 20 on the outer case 10.

Further, the inner case 20 includes the reload prevention hooks 25a and 25b at both sides of the rear end thereof. The reload prevention hooks 25a and 25b engage with the catching protrusions 18a and 18b, respectively. When the inner case 20 is moved rearward, the reload prevention hooks 25a and 25b are fixed to the outer case 10 to prevent the inner case 20 from moving forward.

Figure 5:
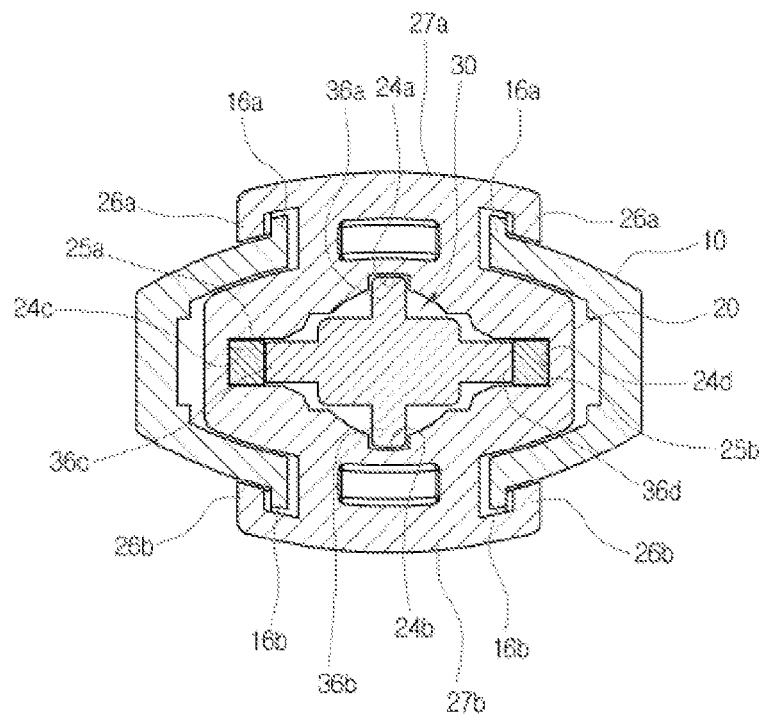
FIG. 5 is a cross-sectional view taken along line V-V of FIG. 1.

Referring to FIG. 5, first to fourth guide recesses 24a, 24b, 24c, and 24d are disposed in the inner case 20. First to fourth guide rails 36a, 36b, 36c, and 36d of the sliding block 30 are slidably coupled to the first to fourth guide recesses 24a, 24b, 24c, and 24d. Under this sliding structure, the sliding block 30 can be straightly moved forward within the inner case 20 without shaking, thereby minimizing a pain caused by the lancet needle 31.

Upper and lower guide holders 27a and 27b are disposed on the top and bottom surfaces of the inner case 20. The upper guide holder 27a includes a pair of the trigger catchers 26a protruding downward from both ends thereof. The lower guide holder 27b includes a pair of the trigger catchers 26b protruding upward from both ends thereof. When the inner case 20 is moved rearward, the trigger catchers 26a and 26b are slid along the guide ribs 16a and 16b of the outer case 10, and are then engaged with the trigger protrusions 17a and 17b. At this point, the sliding block 30 is discharged by elastic force of the coil spring 40. At this point, the trigger catchers 26a and 26b prevent the inner case 20 from moving forward. Thus, after the sliding block 30 is discharged, the sliding block 30 is returned (moved rearward) by resilient force of the coil spring 40, thereby fixing and preventing the lancet needle 31 from being protruded through the through hole 21 of the inner case 20.

Referring to FIGS. 2, 4, and 5, the coil spring 40 elastically supports the sliding block 30 within the outer case 10. The lancet needle 31 is coupled to the sliding block 30 such that the front end of the lancet needle 31 protrudes from the front end of the sliding block 30. The sliding block 30 includes the loading hooks 32a and 32b at both sides of the rear end thereof. The loading hooks 32a and 32b are engaged with the engagement protrusions 22a and 22b of the inner case 20.

The sliding block 30 includes the first to fourth guide rails 36a, 36b, 36c, and 36d on four outer surfaces thereof, respectively. The first to fourth guide rails 36a, 36b, 36c, and 36d are slidably coupled to the first to fourth guide recesses 24a, 24b, 24c, and 24d of the inner case 20 to straightly move the sliding block 30 within the inner case 20. Accordingly, the upper, lower, left, and right parts of the sliding block 30 are coupled to the inner case 20 in a rail manner, so that the sliding block 30 can be stably and correctly aimed and be straightly discharged without shaking or vibration.

In addition to the rail manner, the guide rod 33 having a predetermined length to be inserted in the coil spring 40 is integrally formed with the rear end of the sliding block 30 to prevent shaking and vibration during the discharging of the sliding block 30. The guide rod 33 is slidably inserted in the guide hole 11 of the outer case 10.

The lancet needle 31 is covered with a protective cab 35, so that the lancet needle 31 is prevented from being exposed before being used. When the protective cap 35 is twisted and pulled out of the inner case 20 to use the lancet needle 31, the lancet needle 31 is exposed.

Hereinafter, an operation of the safety lancet according to the first embodiment will now be described with reference to FIGS. 4 to 10.

Figure 6:
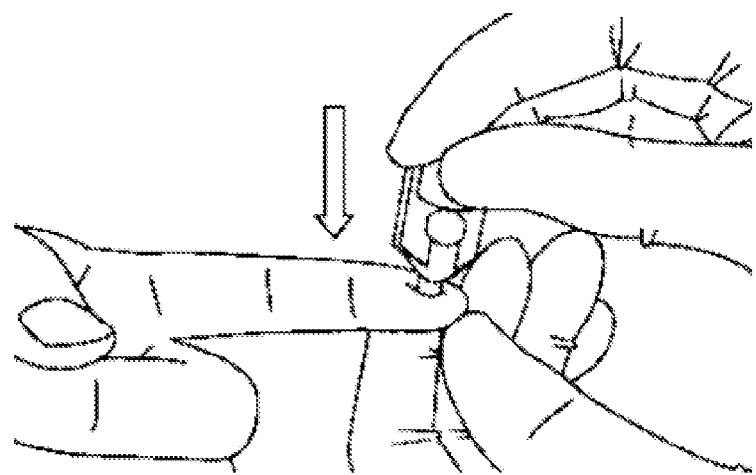
FIG. 6 is a perspective view illustrating a state that the safety lancet is used, according to the first embodiment of the present invention.

First, the protective cap 35 covering the lancet needle 31 is removed from the safety lancet as illustrated in FIG. 4. Then, as illustrated in FIG. 6, the through hole 21 of the inner case 20 is brought into contact with a target portion of a finger, and the outer case 10 held by a user is pressed toward the finger.

Figure 7:
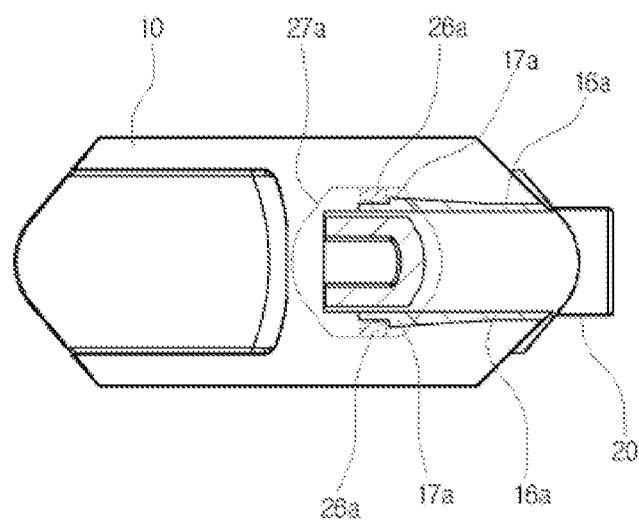
FIGS. 7 to 10 are views illustrating a series of operations of the safety lancet according to the first embodiment of the present invention.

Accordingly, the outer case 10 is moved forward as illustrated in FIG. 7, the inner case 20 is moved rearward, relative to the outer case 10. At this point, the sliding block 30 with the loading hooks 32a and 32b engaged with the engagement protrusions 22a and 22b of the inner case 20 is also moved reward together with the inner case 20.

After that, as the inner case 20 is moved rearward as illustrated in FIG. 8, the trigger catchers 26a and 26b are moved rearward along the guide ribs 16a and 16b, and are engaged with the trigger protrusions 17a. Then, the loading hooks 32a and 32b of the sliding block 30 are inserted into the loading release guide recesses 14a and 14b of the outer case 10, and the distance thereof is increased. Accordingly, the loading hooks 32a and 32b are disengaged from the engagement protrusions 22a and 22b of the inner case 20.

Figure 9:
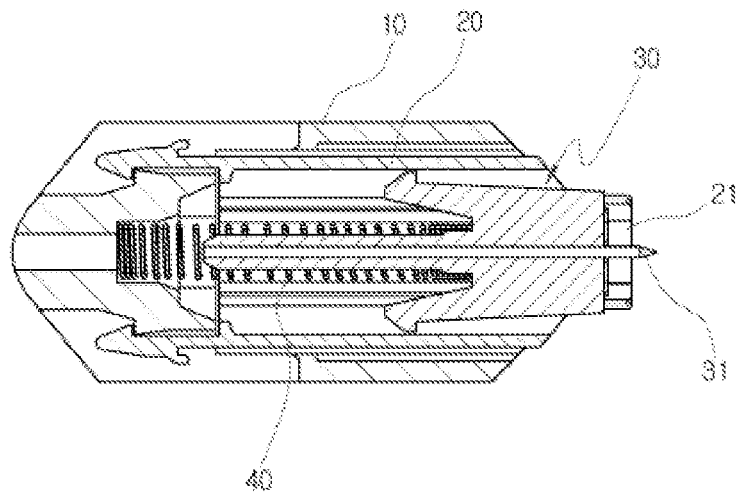

Then, as illustrated in FIG. 9, elastic force of the coil spring 40 compressed by the rear movement of the inner case 20 moves the sliding block 30 forward along the inner case 20 fixed to the outer case 10. At this point, since the first to fourth guide rails 36a, 36b, 36c, and 36d disposed on the four outer surfaces of the sliding block 30 are slid along the first to fourth guide recesses 24a, 24b, 24c, and 24d of the inner case 20 (refer to FIG. 5), the sliding block 30 is straightly moved to the finger without shaking or vibration. The lancet needle 31 is protruded outward through the through hole 21, and is inserted in the target portion of the finger.

Figure 10:
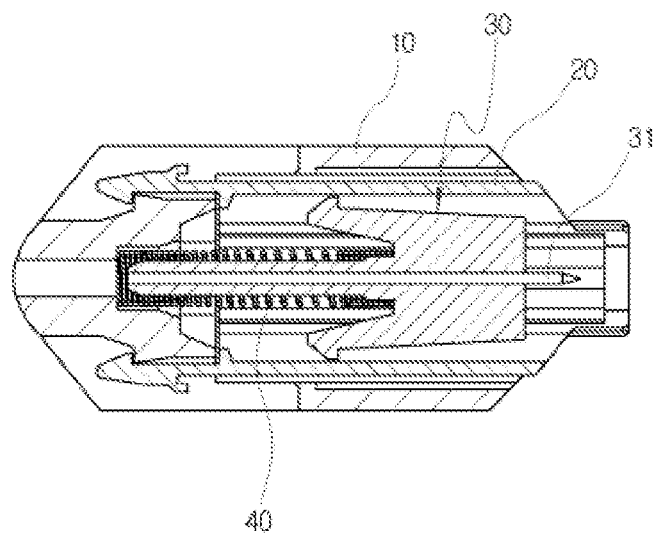

After that, as illustrated in FIG. 10, the sliding block 30 is returned into the inner case 20 by the resilient force of the coil spring 40.

As such, after the safety lancet is used, the inner case 20 is completely fixed to the outer case 10, and the sliding block 30 is prevented from being reloaded on the inner case 20, thereby fundamentally preventing reuse of the safety lancet.

In addition, the sliding block 30 is straightly discharged without shaking, to thereby reduce pain when blood is obtained. In addition, a direction of the safety lancet contacting a target portion such as the end of a finger is the same as a discharged direction of the sliding block 30, and aiming and an incident direction of the safety lancet are uniform, thus further stabilizing a position where blood is obtained, or an insertion depth of the lancet needle 31.

Hereinafter, a safety lancet according to the second to fifth embodiments will now be described with reference to FIGS. to 29. In addition, like reference numerals denote like elements in the first to fifth embodiments, and thus descriptions thereof will be omitted in the following embodiments.

Figure 11:
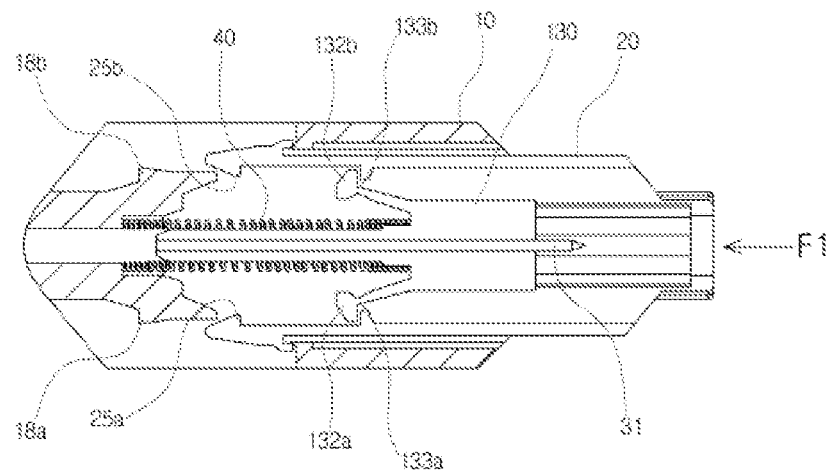
FIG. 11 is a cross-sectional view illustrating a safety lancet according to a second embodiment of the present invention.
Figure 12:
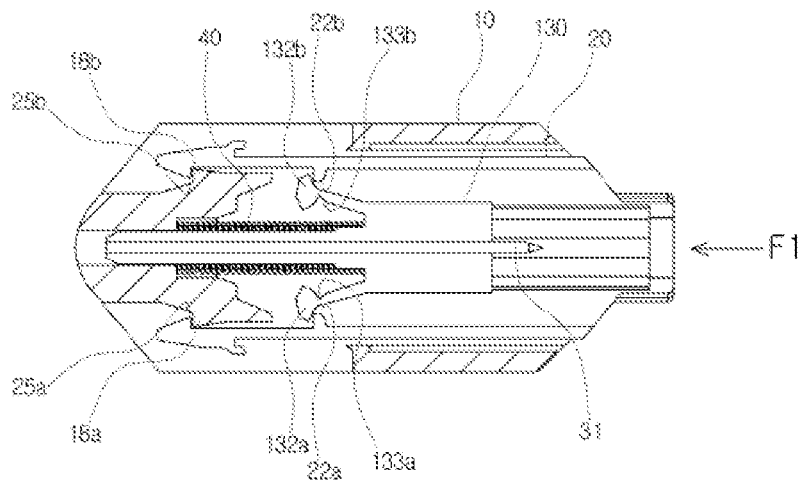
FIGS. 12 to 15 are cross-sectional views illustrating a series of operations of the safety lancet according to the second embodiment of the present invention.

Referring to FIG. 11, a safety lancet according to the second embodiment includes a sliding block 130 having a pair of loading hooks 132a and 132b. Neck parts 133a and 133b of the loading hooks 132a and 132b have a thickness to be broken by a predetermined load.

An operation of the safety lancet according to the second embodiment will now be described with reference to FIGS. 12 to 15.

Referring to FIG. 11, the front end of an inner case 20 is pressed in a direction F1 to use the safety lancet. Accordingly, referring to FIG. 12, the inner case 20 is inserted along an inner portion of an outer case 10, and a pair of reload prevention hooks 25a and 25b of the inner case 20 are caught by catching protrusions 18a and 18b of the outer case 10.

Figure 13:
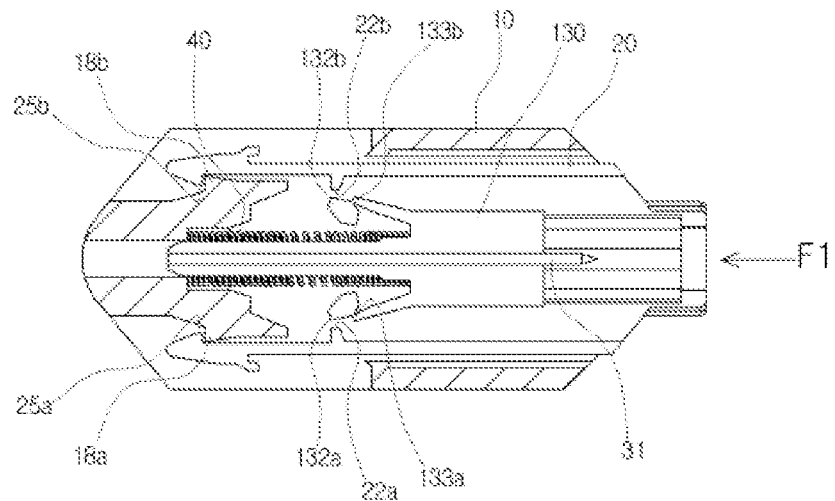

At this point, referring to FIG. 13, a maximum load generated by pressure from a coil spring 40 is applied to the neck parts 133a and 133b of the loading hooks 132a and 132b, and the neck parts 133a and 133b are broken to a state that the safety lancet cannot be reused. Accordingly, the loading hooks 132a and 132b are disengaged from engagement protrusions 22a and 22b of the inner case 20.

Figure 14:
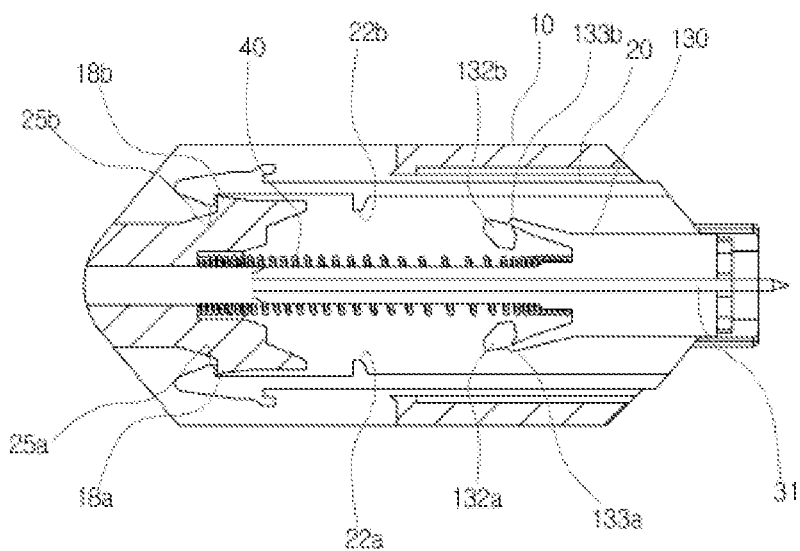

Then, referring to FIG. 14, elastic force of the coil spring 40 compressed by the rear movement of the inner case 20 moves the sliding block 130 forward along the inner case 20 fixed to the outer case 10, and a lancet needle 31 is protruded out of the inner case 20 and is inserted into a target portion of a finger.

Figure 15:
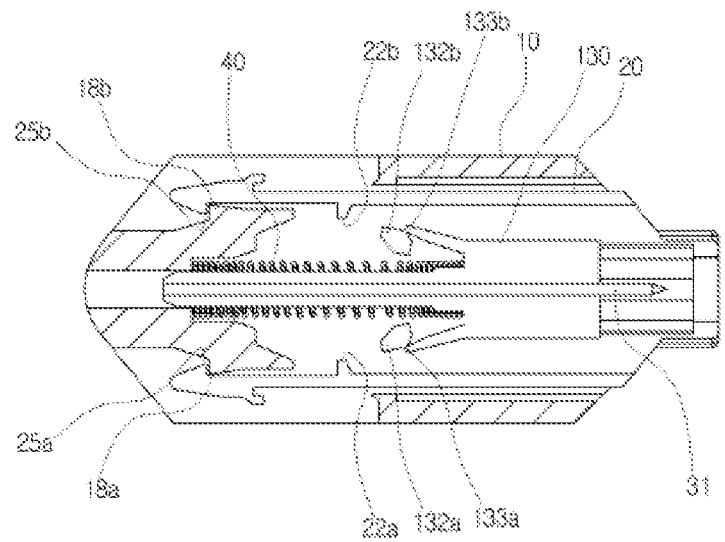

After that, as illustrated in FIG. 15, the sliding block 130 is returned into the inner case 20 by resilient force of the coil spring 40, and the lancet needle 31 is retracted into the inner case 20 for safety.

Figure 16:
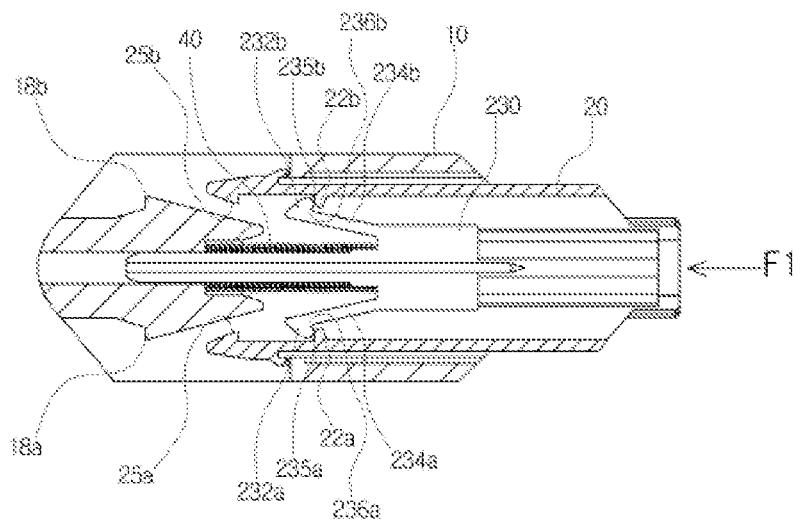
FIG. 16 is a cross-sectional view illustrating a safety lancet according to a third embodiment of the present invention.

Referring to FIG. 16, a safety lancet according to the third embodiment includes a sliding block 230 having a pair of loading hooks 232a and 232b that are disposed on ends of extension bars 234a and 234b extended from the sliding block 230.

Edges 235a and 235b of the loading hooks 232a and 232b are rounded, and edges 236a and 236b of engagement protrusions 22a and 22b of an inner case 20 are rounded.

A predetermined load, generated by a predetermined pressure from a coil spring 40 compressed when the inner case 20 is moved rearward and coupled to an outer case 10, is applied to the sliding block 230 in a direction opposite to a direction F1 (refer to FIG. 16), and the edges 235a and 235b of the loading hooks 232a and 232b are slid along the edges 236a and 236b of the engagement protrusions 22a and 22b, so that the loading hooks 232a and 232b can be easily disengaged from the engagement protrusions 22a and 22b.

Figure 17:
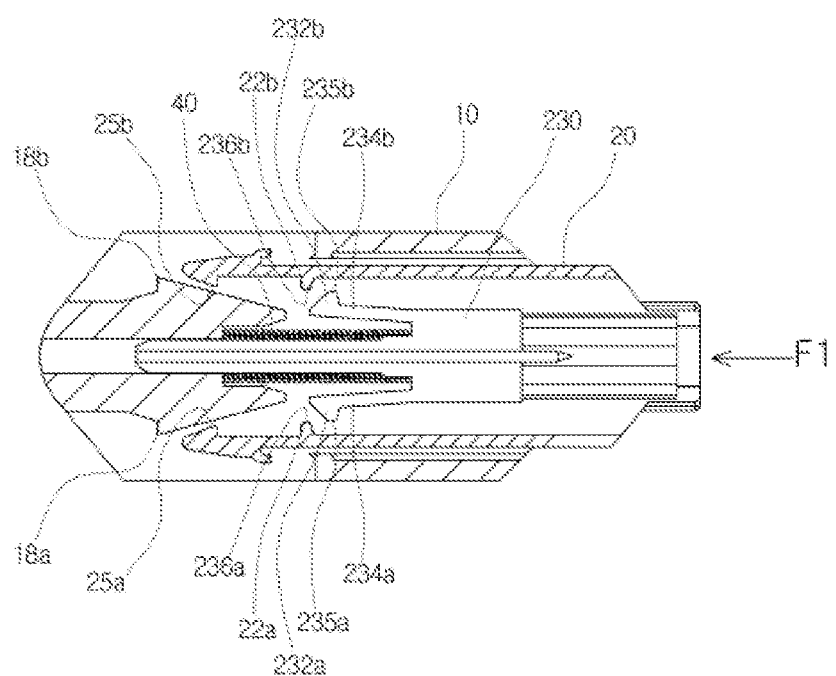
FIGS. 17 to 19 are cross-sectional views illustrating a series of operations of the safety lancet according to the third embodiment of the present invention.

An operation of the safety lancet according to the third embodiment will now be described with reference to FIGS. 17 to 19.

Referring to FIG. 16, the front end of the inner case 20 is pressed in the direction F1 to use the safety lancet. Accordingly, referring to FIG. 17, the inner case 20 is inserted along an inner portion of the outer case 10. At this point, a maximum load generated by a predetermined pressure from the coil spring 40 is applied to the sliding block 230.

Accordingly, the edges 235a and 235b of the loading hooks 232a and 232b are slid along the edges 236a and 236b of the engagement protrusions 22a and 22b, and the distance between the extension bars 234a and 234b is decreased to disengage the loading hooks 232a and 232b from the engagement protrusions 22a and 22b.

After that, the inner case 20 is further moved in the direction F1, and reload prevention hooks 25a and 25b of the inner case 20 are caught by catching protrusions 18a and 18b, respectively.

Figure 18:
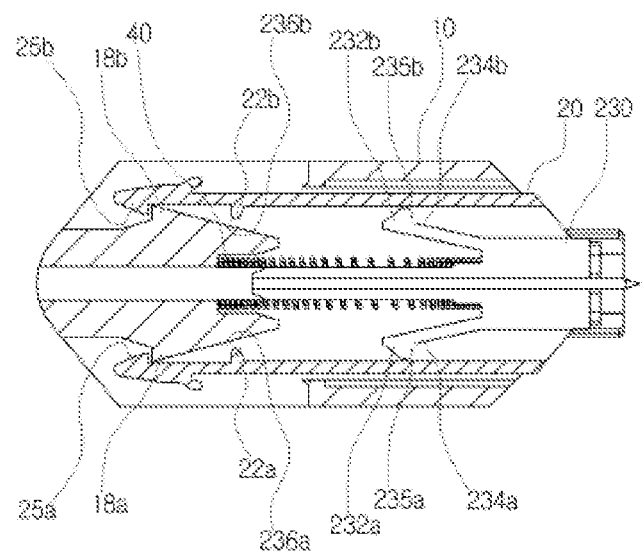

Referring to FIG. 18, elastic force of the coil spring 40 compressed by the rear movement of the inner case 20 moves the sliding block 230 forward along the inner case 20 fixed to the outer case 10, and a lancet needle 31 is protruded out of the inner case 20 and is inserted into a target portion of a finger.

Figure 19:
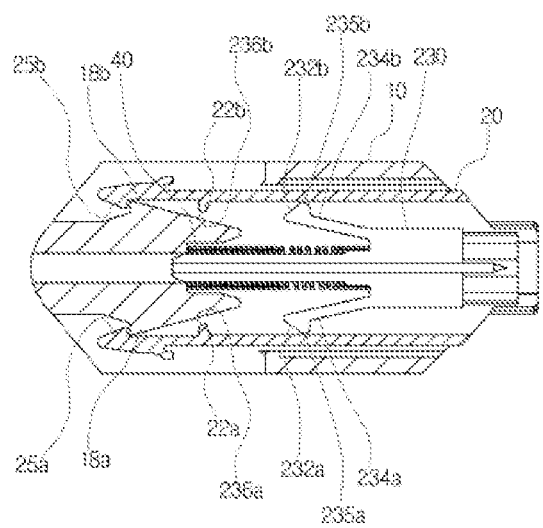

After that, as illustrated in FIG. 19, the sliding block 230 is returned into the inner case 20 by resilient force of the coil spring 40, and the lancet needle 31 is retracted into the inner case 20 for safety, as in the second embodiment.

Figure 20:
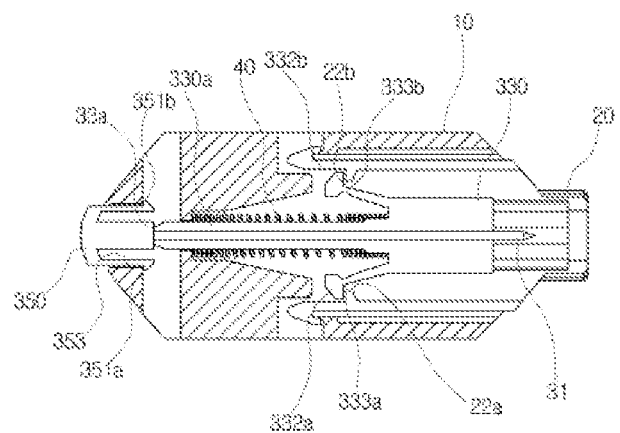
FIG. 20 is a cross-sectional view illustrating a safety lancet according to a fourth embodiment of the present invention.

Referring to FIG. 20, a safety lancet according to the fourth embodiment includes a sliding block 330 having a pair of loading hooks 332a and 332b. Neck parts 333a and 333b of the loading hooks 332a and 332b have a thickness to be broken by a predetermined load, as in the second embodiment.

The sliding block 330 is operated by an operation button 350. The operation button 350 is disposed in a guide hole 353 disposed at the rear end of an outer case 10, and is slid in an axial direction of a guide rod 330a of the sliding block 330. A pair of catching hooks 351a and 351b prevent the operation button 350 from being removed from the outer case 10.

An operation of the safety lancet according to the fourth embodiment will now be described with reference to FIGS. 21 to 24.

Figure 21:
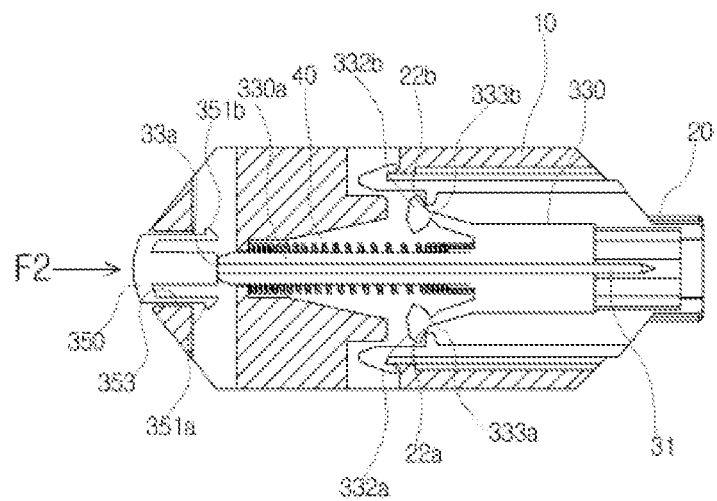
FIGS. 21 to 24 are cross-sectional views illustrating a series of operations of the safety lancet according to the fourth embodiment of the present invention.
Figure 22:
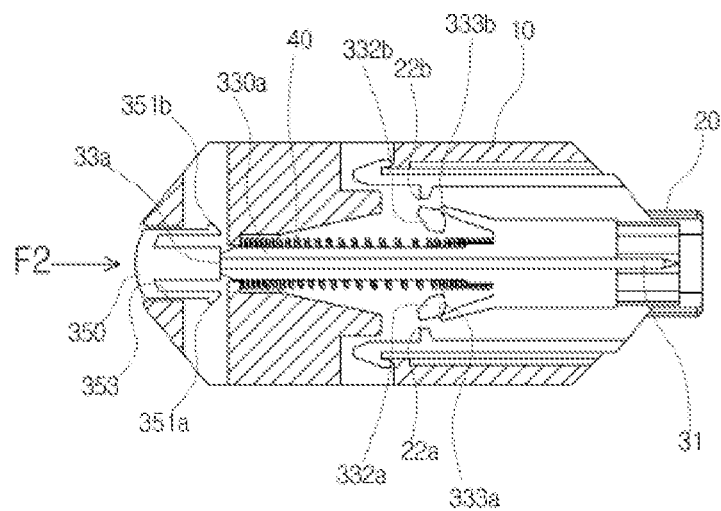

Referring to FIG. 21, when the operation button 350 is pressed in a direction F2 to use the safety lancet, the operation button 350 presses an end of the guide rod 330a in the direction F2. At this point, referring to FIG. 22, the operation button 350 pushes the sliding block 330 in the direction F2, and a maximum load is applied to the neck parts 333a and 333b of the loading hooks 332a and 332b so as to break and the neck parts 333a and 333b to a state that the safety lancet cannot be reused. Accordingly, the loading hooks 332a and 332b are disengaged from engagement protrusions 22a and 22b of the inner case 20.

Figure 23:
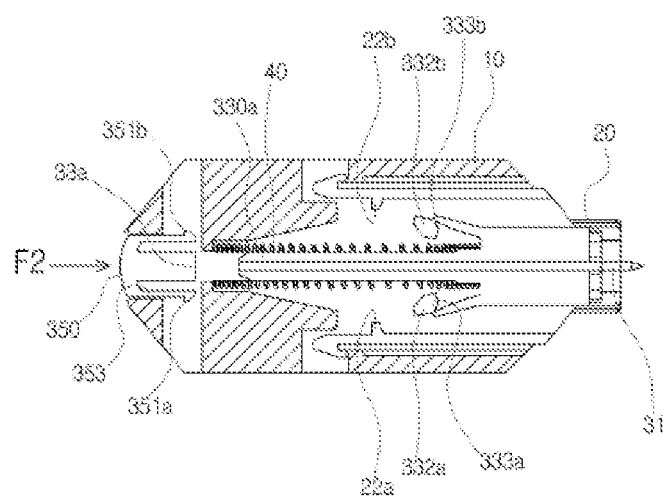

Then, referring to FIG. 23, elastic force of the coil spring 40 compressed by the rear movement of the inner case 20 moves the sliding block 330 forward along the inner case 20 fixed to the outer case 10, and a lancet needle 31 is protruded out of the inner case 20 and is inserted into a target portion of a finger.

Figure 24:
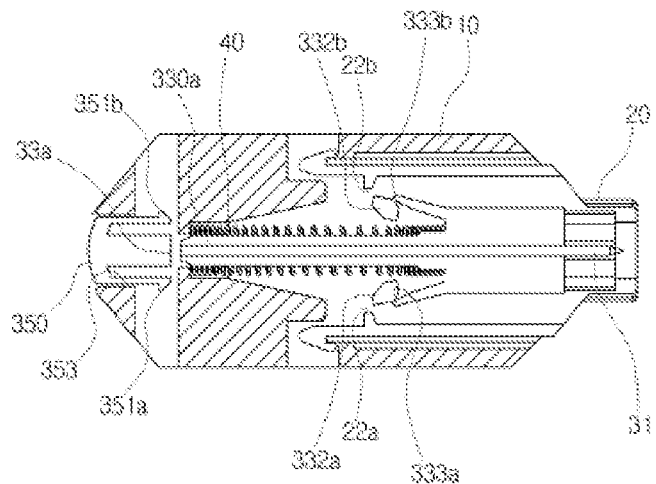

After that, as illustrated in FIG. 24, the sliding block 330 is returned into the inner case 20 by resilient force of the coil spring 40, and the lancet needle 31 is retracted into the inner case 20 for safety.

Figure 25:
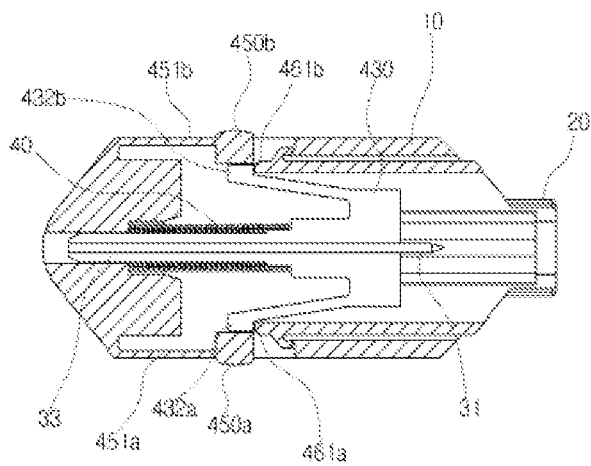
FIG. 25 is a cross-sectional view illustrating a safety lancet according to a fifth embodiment of the present invention.

Referring to FIG. 25, a safety lancet according to the fifth embodiment includes a pair of operation buttons 450a and 450b to operate a sliding block 430, as in the fourth embodiment. The operation buttons 450a and 450b are disposed, respectively, on the front ends of a pair of operation bars 451a and 451b extending from both sides of an outer case 10. The operation bars 451a and 451b are elastically connected to the outer case 10, so that the operation bars 451a and 451b can be pressed in directions F4 and F3, respectively, as illustrated in FIG. 26.

A pair of loading hooks 432a and 432b of the sliding block 430 are caught by catching protrusions 461a and 461b of an inner case 20, respectively, before the safety lancet is operated.

An operation of the safety lancet according to the fifth embodiment will now be described with reference to FIGS. 26 to 29.

Figure 26:
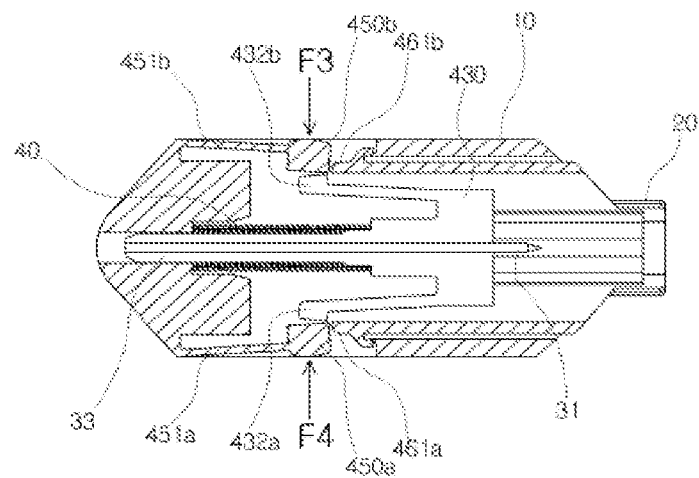
FIGS. 26 to 29 are cross-sectional views illustrating a series of operations of the safety lancet according to the fifth embodiment of the present invention.

When the operation buttons 450a and 450b are pressed in the directions F3 and F4 to use the safety lancet as illustrated in FIG. 26, the loading hooks 432a and 432b are pushed toward a guide rod 33 and are disengaged from the catching protrusions 461a and 461b of the inner case 20.

Figure 27:
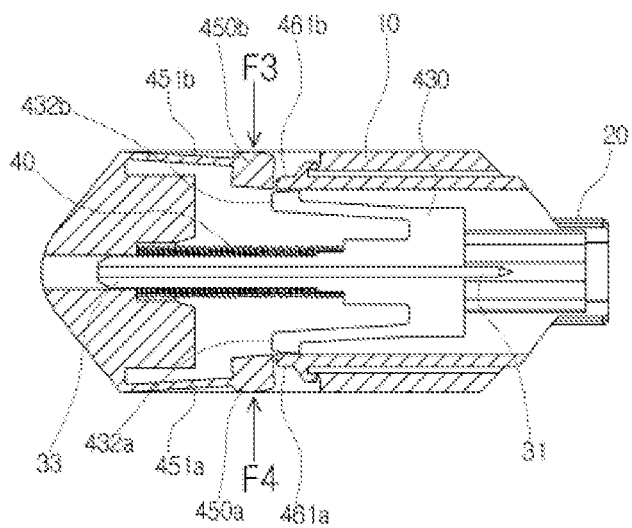
Figure 28:
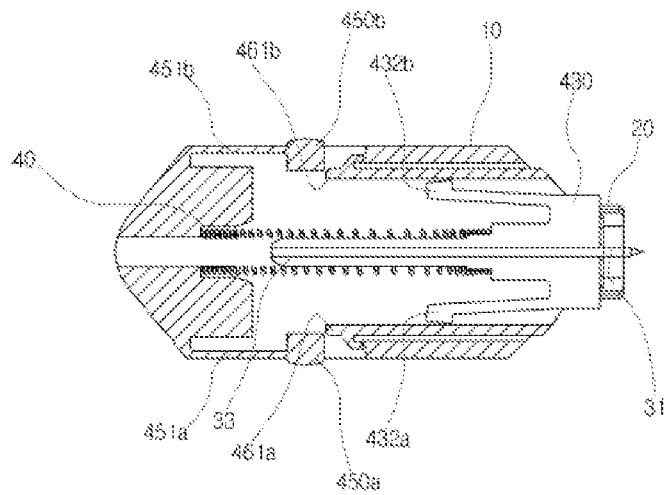

Then, referring to FIG. 27, elastic force of the coil spring 40 compressed by the rear movement of the inner case 20 moves the sliding block 430 forward along the inner case 20 fixed to the outer case 10, and a lancet needle 31 is protruded out of the inner case 20 as illustrated in FIG. 28 and is inserted into a target portion of a finger.

Figure 29:
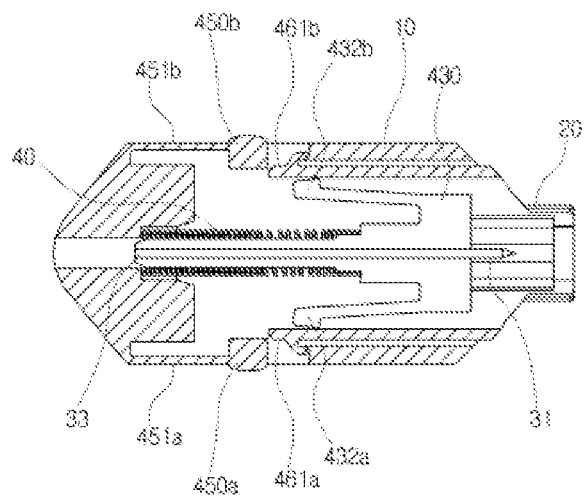
Figure 30:
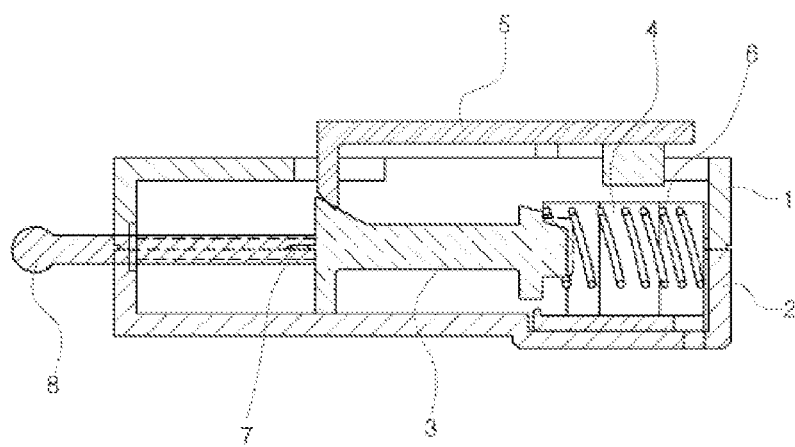
FIG. 30 is a cross-sectional view illustrating a safety lancet in the related art.

After that, as illustrated in FIG. 29, the sliding block 430 is returned into the inner case 20 by resilient force of the coil spring 40, and the lancet needle 31 is retracted into the inner case 20 for safety.

According to the embodiments, an outer case includes catching protrusions that engage with reload prevention hooks of an inner case in a position where coupling hooks of the inner case are disengaged from engagement protrusions of the outer case. When the reload prevention hooks are fixed to the catching protrusions, movement of the inner case is difficult. Thus, a reload double prevention structure prevents a sliding block from being reloaded in a trigger position, thereby improving safety of a safety lancet.

In addition, the sliding block is straightly discharged without shaking, to thereby reduce pain when blood is obtained. In addition, a direction of the safety lancet contacting a target portion such as the end of a finger is the same as a discharged direction of the sliding block, and aiming and an incident direction of the safety lancet are uniform, thus further stabilizing a position where blood is obtained, or an insertion depth of a lancet needle.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A safety lancet comprising:
    an outer case having
        a first hollow inner chamber formed inside a front portion of the outer case,
        a guide hole formed in a rear portion of the outer case,
        loading release guide recesses formed around the guide hole in the rear portion of the outer case and open to the first hollow inner chamber, and
        catching protrusions disposed on opposing lateral sides of the rear portion of the outer case;
    an inner case slidingly moving in the first hollow inner chamber of the outer case and having
        a second hollow inner chamber inside the inner case,
        a pair of reload prevention hooks formed on opposing lateral sides of a rear end of the inner case and protruding inwardly for engaging with the catching protrusions,
        engagement protrusions formed on an interior wall of the inner case, and
        a through hole formed in a front end of the inner case;
    a sliding block slidingly moving in the second hollow inner chamber of the inner case and having
        a lancet needle protruding from a front end of the sliding block,
        a pair of loading hooks formed on opposing lateral sides of a rear end of the sliding block to engage with the engagement protrusions of the inner case, and
        neck parts connecting the pair of loading hooks to the sliding block;
    a guide rod disposed in the rear end of of the sliding block and slidingly inserted into the guide hole of the outer case; and
    a coil spring surrounding the guide rod of the sliding block,
    wherein as the inner case is moved rearward along the first hollow inner chamber of the outer case and the pair of loading hooks of the sliding block are inserted into the loading release guide recesses, the pair of loading hooks of the sliding block is disengaged from the engagement protrusions of the inner case and the sliding block is moved forward by elastic force of the coil spring to temporarily expose the lancet needle out of the inner case, and is then moved rearward to the inner case by resilient force of the coil spring.

2. The safety lancet of claim 1, wherein the inner case further comprises:
    a pair of coupling hooks formed on opposing lateral sides of the rear end of the inner case and protruding outwardly to couple to the outer case, and
    a pair of guide holders protruding outwardly on outer top and bottom surfaces thereof, respectively, wherein each of the guide holders comprises a pair of trigger catchers protruding from opposing lateral sides of the guide holders, and
    wherein the outer case further comprises
        guide ribs formed on outer top and bottom surfaces thereof to guide the trigger catchers of the inner case, and
        trigger protrusions disposed on rear ends of the guide ribs and caught by the trigger catchers of the inner case.

3. The safety lancet of claim 2, wherein when the inner case is moved rearward such that the trigger catchers are moved along the guide ribs and are engaged with the trigger protrusions of the outer case, the elastic force of the coil spring is applied to the sliding block.

4. The safety lancet of claim 3, wherein when the sliding block is moved rearward within a certain time after the inner case is moved rearward, the loading release guide recesses guide the loading hooks of the sliding block to decrease a distance therebetween, thereby disengaging the loading hooks from the engagement protrusions of the inner case.

5. The safety lancet of claim 2, wherein when the inner case is moved rearward such that the trigger catchers are moved along the guide ribs and are disengaged from the trigger protrusions of the outer case, the elastic force of the coil spring is applied to the sliding block to break the neck parts of the loading hooks of the sliding block, thereby disengaging the loading hooks of the sliding block from the engagement protrusions of the inner case.

6. The safety lancet of claims 5, wherein the guide rod has a rod shape and is integrally formed with the rear end of the sliding block, and
    wherein a spring fixing recess is disposed in the rear portion of the outer case such that an end of the coil spring is inserted and fixed in the spring fixing recess.

7. The safety lancet of claim 2, wherein edges of the loading hooks are rounded, and edges of the engagement protrusions engaging with the loading hooks are rounded,
    wherein when the inner case is moved rearward such that the trigger catchers are moved along the guide ribs and are engaged with the trigger protrusions of the outer case, the elastic force of the coil spring is applied to the sliding block to slide the edges of the loading hooks along the edges of the engagement protrusions, thereby disengaging the loading hooks of the sliding block from the engagement protrusions of the inner case.

8. The safety lancet of claims 7, wherein the guide rod has a rod shape and is integrally formed with the rear end of the sliding block, and
    wherein a spring fixing recess is disposed in the rear portion of the outer case such that an end of the coil spring is inserted and fixed in the spring fixing recess.
    wherein a spring fixing recess is disposed in the rear portion of the outer 9. The safety lancet of claim 2, wherein the outer case comprises a pair of operation buttons extending from both sides thereof and elastically connected thereto, and
    the operation buttons press the loading hooks to decrease a distance therebetween, thereby disengaging the loading hooks from catching protrusions disposed on both sides of the inner case.

10. The safety lancet of claim 9, wherein the guide rod has a rod shape and is integrally formed with the rear end of the sliding block, and wherein a spring fixing recess is disposed in the rear portion of the outer case such that an end of the coil spring is inserted and fixed in the spring fixing recess. case such that an end of the coil spring is inserted and fixed in the spring fixing recess.

11. The safety lancet of claims 3, wherein the guide rod has a rod shape and is integrally formed with the rear end of the sliding block, and wherein a spring fixing recess is disposed in the rear portion of the outer case such that an end of the coil spring is inserted and fixed in the spring fixing recess.

12. The safety lancet of claims 1, wherein the guide rod has a rod shape and is integrally formed with the rear end of the sliding block, and wherein a spring fixing recess is disposed in the rear portion of the outer case such that an end of the coil spring is inserted and fixed in the spring fixing recess.

13. The safety lancet of claim 12, wherein the outer case comprises an operation button on the rear portion thereof to press the guide rod and move the sliding block forward, and the forward movement of the sliding block breaks the neck parts of the loading hooks of the sliding block, thereby disengaging the loading hooks of the sliding block from the engagement protrusions of the inner case.

14. The safety lancet of claim 1, wherein after moving forward, the sliding block is returned into the inner case by the resilient force of the coil spring to retract the lancet needle into the inner case.

15. The safety lancet of claim 1, wherein the sliding block comprises first to fourth guide rails on an outer surface thereof and the inner case comprises first to fourth guide recesses in the interior wall thereof, and the first to fourth guide rails are slidably coupled to the first to fourth guide recesses.

* * * * *